United States Patent
Kanno

(10) Patent No.: US 9,051,298 B2
(45) Date of Patent: Jun. 9, 2015

(54) METHOD FOR MANUFACTURING 4-BENZYL-1-METHYL-6-OXABICYCLO[3,2,0]HEPTANE DERIVATIVE AND METHOD FOR MANUFACTURING AZOLE DERIVATIVE

(71) Applicant: Kureha Corporation, Chuo-ku Tokyo (JP)

(72) Inventor: Hisashi Kanno, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 14/357,058

(22) PCT Filed: Nov. 5, 2012

(86) PCT No.: PCT/JP2012/078658
§ 371 (c)(1),
(2) Date: May 8, 2014

(87) PCT Pub. No.: WO2013/069614
PCT Pub. Date: May 16, 2013

(65) Prior Publication Data
US 2014/0336389 A1    Nov. 13, 2014

(30) Foreign Application Priority Data
Nov. 11, 2011    (JP) ................................ 2011-247990

(51) Int. Cl.
*C07D 249/08* (2006.01)
*C07D 233/60* (2006.01)
*C07D 405/06* (2006.01)

(52) U.S. Cl.
CPC ............ *C07D 405/06* (2013.01); *C07D 249/08* (2013.01)

(58) Field of Classification Search
CPC ... C07D 233/56; C07D 249/12; C07D 305/14
USPC .......................................... 548/311.4, 268.8
See application file for complete search history.

(56) References Cited

U.S. PATENT DOCUMENTS

| 7,354,922 B2 | 4/2008 | Xiao et al. |
| 8,710,090 B2 | 4/2014 | Araki et al. |
| 2006/0258665 A1 | 11/2006 | Xiao et al. |
| 2012/0232286 A1* | 9/2012 | Araki et al. ............... 548/267.4 |

FOREIGN PATENT DOCUMENTS

CN    101115753 A    1/2008

OTHER PUBLICATIONS

Yakhak Hoechi, "An Approach to the Enantioselective Synthesis of the Crucial Intermediate of Conformationally Locked Nucleosides", 2010, Vol54(6), p. 474-480.
International Search Report of PCT/JP2012/078659 dated Dec. 25, 2012.
English translation of International Preliminary Report on Patentability and Written Opinion issued May 22, 2014, in PCT International Application No. PCT/JP2012/078658.
Chinese Office Action dated Feb. 16, 2015 for Application No. 201280053420.5 with English language translation.
Extended European Search Report for Application No. 12847713.0, dated Mar. 10, 2015.

* cited by examiner

*Primary Examiner* — Rebecca Anderson
*Assistant Examiner* — Karen Cheng
(74) *Attorney, Agent, or Firm* — Birch, Stewart, Kolasch & Birch, LLP

(57) ABSTRACT

In order to manufacture a higher yield of a 4-benzyl-1-methyl-6-oxabicyclo[3,2,0]heptane derivative, the present invention is a method for manufacturing a compound represented by General Formula (I) which includes a step for reducing a compound represented by General Formula (II) using a hydride-type reducing agent in an aprotic solvent having an amide bond.

8 Claims, No Drawings

METHOD FOR MANUFACTURING 4-BENZYL-1-METHYL-6-OXABICYCLO[3,2,0]HEPTANE DERIVATIVE AND METHOD FOR MANUFACTURING AZOLE DERIVATIVE

TECHNICAL FIELD

The present invention relates to a novel method for manufacturing 4-benzyl-1-methyl-6-oxabicyclo[3,2,0]heptane derivatives used as an intermediate in agrochemicals and to a method for manufacturing an azole derivative which encompasses this novel manufacturing method.

BACKGROUND ART

Patent Document 1 describes a 2-(halogenated hydrocarbon-substituted)-5-benzyl-1-azolylmethylcyclopentanol derivative which is a compound that can be used as an active ingredient in agricultural and horticultural agents and in industrial material protecting agents. A method is described in the same document, as a step in the method for manufacturing this derivative, in which a 4-benzyl-1-methyl-6-oxabicyclo[3,2,0]heptane derivative (intermediate compound) is obtained by oxetane-cyclizing and sulfonic acid-esterifying a 2,2-bis(hydroxymethyl)cyclopentanol derivative, and then reducing the resulting sulfonic acid-esterified oxetane derivative.

PRIOR ART DOCUMENTS

Patent Documents

Patent Document 1

International Publication WO2011/070771 (Published Jun. 16, 2011).

SUMMARY OF THE INVENTION

Problem Solved by the Invention

However, in order to mass-produce a 2-(halogenated hydrocarbon-substituted)-5-benzyl-1-azolylmethylcyclopentanol derivative inexpensively, the yield of the step in which the sulfonic acid-esterified oxetane derivative is reduced to obtain the 4-benzyl-1-methyl-6-oxabicyclo[3,2,0]heptane derivative has to be improved.

In view of these problems, it is an object of the present invention to provide a method for manufacturing a higher yield of the 4-benzyl-1-methyl-6-oxabicyclo[3,2,0]heptane derivative serving as an intermediate compound.

Means of Solving the Problem

The present inventor conducted extensive research in order to solve these problems. As a result, he discovered that the intermediate compounds of 4-benzyl-1-methyl-6-oxabicyclo[3,2,0]heptane derivatives were unstable, that there were conditions under which the intermediate compounds could be reduced at relatively low temperatures, and that 4-benzyl-1-methyl-6-oxabicyclo[3,2,0]heptane derivatives could be manufactured at a higher yield using these conditions. The present invention is a product of these discoveries. The present invention is based on these novel findings and includes the following.

The present invention is a method for manufacturing a compound represented by General Formula (I) below.

Formula 1

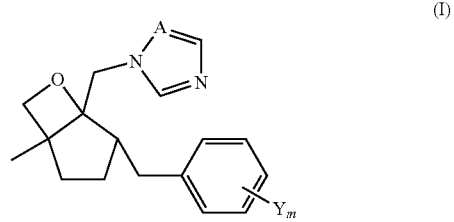
(I)

In General Formula (I), Y represents a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms, or a phenyl group, m represents an integer from 0 to 5, Y being the same or different when m is an integer equal to or greater than 2, and A represents a nitrogen atom or a methine group.

This method includes a step for reducing a compound represented by General Formula (II) below using a hydride-type reducing agent in an aprotic solvent having an amide bond or a mixed solvent including the aprotic solvent.

Formula 2

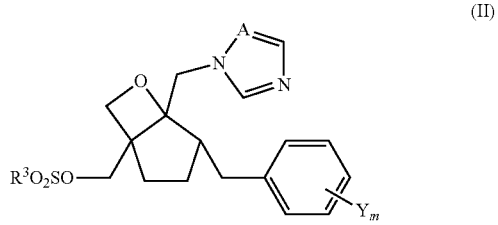
(II)

In General Formula (II), Y, m and A are the same as Y, m and A in General Formula (I), respectively, $R^3$ represents an alkyl group having 1 to 3 carbon atoms, a haloalkyl group having 1 to 3 carbon atoms, a substitutable phenyl group, or a substitutable naphthyl group.

The present invention is also a method for manufacturing an azole derivative represented by General Formula (V) below:

Formula 3

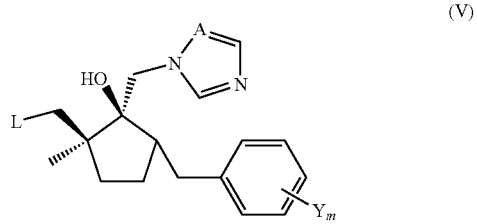
(V)

In General Formula (V), Y, m and A are the same as Y, m and A in General Formula (I), respectively, and L represents a halogen atom.

This method includes the manufacturing method described above, and the azole derivative is obtained by reacting a compound represented by General Formula (I) above with a halogen atom Effect of the Invention The present invention has the effect of being able to manufacture a higher yield of 4-benzyl-1-methyl-6-oxabicyclo[3,2,0]heptane derivatives.

BEST MODE FOR CARRYING OUT THE INVENTION

The following is an explanation of the manufacturing method in an embodiment of the present invention.

The manufacturing method in the present embodiment is a method for manufacturing a 4-benzyl-1-methyl-6-oxabicyclo[3,2,0]heptane derivative represented by General Formula (I) below (referred to below as Compound (I)). This method includes a step for reducing a compound represented by General Formula (II) below (referred to below as Compound (II)) using a hydride-type reducing agent in an aprotic solvent having an amide bond or a mixed solvent including the aprotic solvent.

Formula 4

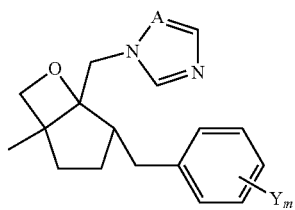
(I)

In General Formula (I), Y represents a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms, or a phenyl group, m represents an integer from 0 to 5, Y being the same or different when m is an integer equal to or greater than 2, and A represents a nitrogen atom or a methine group.

Formula 5

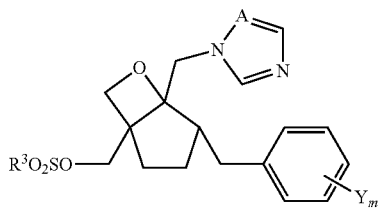
(II)

In General Formula (II), Y, m and A are the same as Y, m and A in General Formula (I), respectively, $R^3$ represents an alkyl group having 1 to 3 carbon atoms, a haloalkyl group having 1 to 3 carbon atoms, a substitutable phenyl group, or a substitutable naphthyl group.

The following is a more detailed description of Compound (I).

Solvent

The aprotic solvent having an amide bond can be N-methyl-2-pyrrolidinone (NMP), N,N-dimethylacetamide (DMA), and N,N-dimethylformamide. Among these, N-methyl-2-pyrrolidinone and N,N-dimethylacetamide are preferred.

The mixed solvent including an aprotic solvent having an amide bond can be a mixture in which the aprotic solvent is mixed with another solvent. These solvents include halogenated hydrocarbons such as dichloromethane, chloroform and dichloroethane, aromatic hydrocarbons such as benzene, toluene and xylene, aliphatic hydrocarbons such as petroleum ether, hexane and methyl cyclohexane, ethers such as diethyl ether, tetrahydrofuran and dioxane, and alcohols such as isopropyl alcohol, tert-butanol, methanol and ethanol. Others include water, acetonitrile, and dimethyl sulfoxide.

Hydride-Type Reducing Agent

Hydride-type reducing agents used in the manufacturing method of the present embodiment include borohydride compounds such as diborane, sodium borohydride, lithium borohydride, sodium trimethoxyborohydride, sodium cyanoborohydride, lithium triethylborohydride, potassium borohydride, zinc borohydride, sodium acetoxyborohydride and borane-tetrahydrofuran complexes, as well as aluminum hydride compounds such as lithium aluminum hydride, sodium bis(2-methoxyethoxy) aluminum hydride, sodium aluminum hydride, and diisobutylaluminum hydride. Among these, sodium borohydride, lithium borohydride, sodium trimethoxyborohydride, lithium aluminum hydride, and sodium bis(2-methoxyethoxy) aluminum hydride are preferred. Sodium borohydride is especially preferred.

The amount of hydride-type reducing agent used is usually from 0.2 to 20 times, and preferably from 0.3 to 10 times, the amount of Compound (II) in terms of the mole ratio. When the reducing agent is sodium borohydride, the amount is usually from 0.2 to 10 times, and preferably 0.3 to 5 times in terms of the mole ratio.

Reaction Conditions

In the manufacturing method of the present embodiment, a reduction reaction can be performed on Compound (II) at a relatively low temperature by using an aprotic solvent having an amide bond as the solvent and by using a hydride-type reducing agent as the reducing agent. In other words, the reaction temperature in the reduction step is usually from −100° C. to 150° C., preferably from −50° C. to 100° C., and more preferably from −50° C. to 70° C. Compound (II) is an unstable compound. When Compound (II) is subjected to heat, the breakdown of Compound (II) is accelerated. As a result, the yield of Compound (I) is reduced. Because the reduction reaction is performed at a relatively low temperature, the manufacturing method in the present embodiment inhibits the breakdown of Compound (II). As a result, the yield of Compound (I) can be increased. After the reduction reaction has been performed at a relatively low temperature, the reduction reaction of the remaining materials can be expedited by applying heat.

The reaction time in the reduction step can be set freely. It usually ranges from 0.1 hours to 3 days, and preferably ranges from 0.5 hours to 2 days.

Compound (I)

A 4-benzyl-1-methyl-6-oxabicyclo[3,2,0]heptane derivative obtained using the manufacturing method of the present embodiment is Compound (I) represented by General Formula (I). The following is a description of Compound (I):

Formula 6

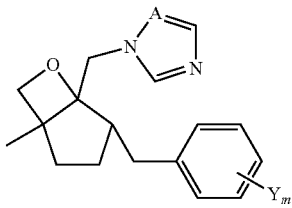

(I)

In General Formula (I), Y represents a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms, or a phenyl group.

Examples of halogen atoms represented by Y include fluorine atoms, chlorine atoms, bromine atoms, and iodine atoms. Among these, fluorine atoms, chlorine atoms and bromine atoms are preferred, and chlorine atoms are more preferred.

Specific examples of alkyl groups having 1 to 4 carbon atoms that are represented by Y include a methyl group, ethyl group, n-propyl group, isopropyl group, n-butyl group, isobutyl group, sec-butyl group and tert-butyl group. Among these an alkyl group having 1 to 3 carbon atoms is preferred, an alkyl group having 1 to 2 carbon atoms is more preferred, and a methyl group is even more preferred.

A haloalkyl group having 1 to 4 carbon atoms represented by Y is an alkyl group in which one or more hydrogen atoms have been substituted by a halogen atom. Examples include a dichloromethyl group, trichloromethyl group, 2-chloroethyl group, 1-chloroethyl group, 2,2-dichloroethyl group, 1,2-dichloroethyl group, 2,2,2-trichloroethyl group, 3-chloropropyl group, 2,3-dichloropropyl group, 1-chloro-1-methylethyl group, 2-chloro-1-methylethyl group, 2-chloropropyl group, 4-chlorobutyl group, fluoromethyl group, difluoromethyl group, trifluoromethyl group, 2-fluoroethyl group, 1-fluoroethyl group, 2,2-difluoroethyl group, 1,2-difluoroethyl group, 2,2,2-trifluoroethyl group, 3-fluoropropyl group, 2,3-difluoropropyl group, 1-fluoro-1-methylethyl group, 2-fluoro-1-methylethyl group, 2-fluoropropyl group, 3,3,3-trifluoropropyl group, 2,2,3,3-tetrafluoropropyl group, 2,2,3,3,3-pentafluoropropyl group, 4-fluorobutyl group, dibromomethyl group, tribromomethyl group, 2-bromoethyl group, 2,2-dibromoethyl group, 1,2-dibromoethyl group, 2,2,2-tribromoethyl group, 3-bromopropyl group, 2,3-dibromopropyl group, 1-bromo-1-methylethyl group, 2-bromo-1-methylethyl group, 2-bromopropyl group, diiodomethyl group, 2,2-diiodoethyl group, 1,2-diiodoethyl group, 2,2,2-triiodoethyl group, 2,3-diiodopropyl group, 1-iodo-1-methylethyl group, and 2-iodo-1-methylethyl group. Among these, a haloalkyl group having 1 to 3 carbon atoms is preferred, a haloalkyl group having 1 to 2 carbon atoms is more preferred, and a trihaloalkyl group having 1 carbon atom is even more preferred.

Specific examples of alkoxy groups having 1 to 4 carbon atoms that are represented by Y include a methoxy group, ethoxy group, and n-propoxy group. Among these, an alkoxy group having 1 to 3 carbon atoms is preferred, an alkoxy group having 1 to 2 carbon atoms is more preferred, and a methoxy group is even more preferred.

A haloalkoxy group having 1 to 4 carbon atoms represented by Y is an alkoxy group substituted by one or more halogen atoms that are the same or different. Examples include a trifluoromethoxy group, difluoromethoxy group, 1,1,2,2,2-pentafluoroethoxy group and 2,2,2-trifluoroethoxy group. Among these, a haloalkoxy group having 1 to 3 carbon atoms is preferred, a haloalkoxy group having 1 to 2 carbon atoms is more preferred, and a dihalomethoxy group or trihalomethoxy group having 1 carbon atom is even more preferred.

As defined above, Y is preferably a halogen atom, methyl group, trifluoromethyl group, trifluoromethoxy group, or difluoromethoxy group. Among these, a halogen atom is more preferred, and a chlorine atom is especially preferred.

In General Formula (I), m represents an integer from 0 to 5. Here, m is preferably an integer from 0 to 3, more preferably an integer from 0 to 2, and even more preferably 0 or 1. When m is an integer that is equal to or greater than 2, Y may be the same or different. When m is an integer that is equal to or greater than 1, Y may be located anywhere from the 2- to the 6-position of the benzene ring. When m is 1, Y may be located in the 4-position of the benzene ring.

In General Formula (I), A is a nitrogen atom or methine group, and preferably a nitrogen atom.

In Compound (I), m is preferably an integer from 0 to 3. When m is an integer that is equal to or greater than 1, Y preferably represents a halogen atom, an alkyl group having 1 to 3 carbon atoms, a haloalkyl group having 1 to 3 carbon atoms, an alkoxy group having 1 to 3 carbon atoms, or a haloalkoxy group having 1 to 3 carbon atoms, and A preferably represents a nitrogen atom. In Compound (I), m is more preferably an integer from 0 to 2. When m is 1 or 2, Y preferably represents a halogen atom, and A preferably represents a nitrogen atom.

Compound (II)

The compound used as the starting material in the manufacturing method of the present embodiment is Compound (II) represented by General Formula (II) below. The following is a description of Compound (II):

Formula 7

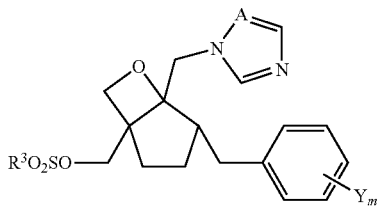

(II)

In General Formula (II), Y, m and A are the same as Y, m and A in General Formula (I), respectively.

$R^3$ represents an alkyl group having 1 to 3 carbon atoms, a haloalkyl group having 1 to 3 carbon atoms, a substitutable phenyl group, or a substitutable naphthyl group. Among these, an alkyl group having 1 to 3 carbon atoms or a haloalkyl group having 1 to 3 carbon atoms is preferred.

Specific examples of alkyl groups having 1 to 3 carbon atoms that are represented by $R^3$ include a methyl group, ethyl group, n-propyl group and isopropyl group. Among these, a methyl group is preferred.

Haloalkyl groups having 1 to 3 carbon atoms that are represented by $R^3$ are alkyl groups in which one or more hydrogen atoms have been substituted by halogen atoms. When two or more hydrogen atoms have been substituted by halogen atoms, the halogen atoms can be the same or different. Halogen atoms include fluorine atoms, chlorine atoms, bromine atoms and iodine atoms. Among these, fluorine atoms and chlorine atoms are preferred. An example of a haloalkyl group is a trifluoromethyl group.

Substituents for the substitutable phenyl groups and substitutable naphthyl groups include halogen atoms, methyl groups, trifluoromethyl groups, nitro groups, and amino groups. Halogen atoms include fluorine atoms, chlorine atoms, bromine atoms and iodine atoms. There are no particular restrictions on the locations and number of substituents for the phenyl groups and naphthyl groups. Specific examples of substituents for the substitutable phenyl groups and substitutable naphthyl groups include 4-methylphenyl groups, 2-methylphenyl groups and 4-chlorophenyl groups.

There are no particular restrictions on the sulfonyloxy group (—$OSO_2R^3$) bonded to the cyclopentane ring of Compound (II) as long as $R^3$ satisfies the definition. Examples include a methanesulfonyloxy group, ethanesulfonyloxy group, propanesulfonyloxy group, trifluoromethanesulfonyloxy group, benzenesulfonyloxy group, 4-chlorobenzenesulfonyloxy group, p-toluenesulfonyloxy group, naphthalene-sulfonyloxy group, and dimethylaminonaphthylsulfonyloxy group. Among these, a methanesulfonyloxy group is preferred.

Manufacturing Method for Compound (II)

There are no particular restrictions on the method used to manufacture Compound (II). However, Compound (II) is preferably obtained (in the ring-closing step) by reacting a compound represented by General Formula (III) (referred to as Compound (III) below) with a base in a solvent.

Formula 8

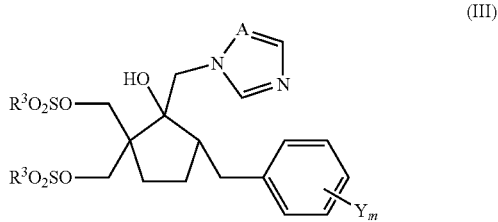

(III)

In General Formula (III), Y, m and A are the same as Y, m and A in General Formula (I), respectively, $R^3$ is the same as $R^3$ in General Formula (II).

Preferred examples of bases used in the reaction in the ring-closing step include alkali metal hydrogen compounds such as sodium hydroxide and lithium hydroxide, and alkali metal alkoxides such as sodium methoxide, sodium ethoxide, sodium t-butoxide and potassium t-butoxide. Other examples include alkali metal hydroxides such as sodium hydroxide and potassium hydroxide, alkali metal carbonates such as sodium carbonate and potassium carbonate, alkaline-earth metal hydroxides such as barium hydroxide and calcium hydroxide, and alkaline-earth metal carbonates such as barium carbonate and calcium carbonate. Among these, alkali metal hydroxides such as sodium hydroxide and potassium hydroxide, alkali metal carbonates such as sodium carbonate and potassium carbonate, alkali metal hydrogen compounds, and alkoxides of alkali metals are preferred. Sodium hydroxide, sodium hydride, sodium t-butoxide, and potassium t-butoxide are especially preferred.

Here, when alkali metal hydroxides such as sodium hydroxide and potassium hydroxide, and alkali metal carbonates such as sodium carbonate and potassium carbonate are used as the base, they may also be used as the aqueous solution.

The amount of base used is usually from 0.5 to 5 times, and preferably from 0.8 to 2 times, the amount of Compound (III) in terms of the mole ratio.

Examples of solvents used in the reaction in the ring-closing step include aprotic solvents having an amide bond, ether-based solvents such as tetrahydrofuran and dimethoxyethane, and mixed solvents including other solvents in addition to these. Other solvents in the mixture include halogenated hydrocarbons such as dichloromethane, chloroform and dichloroethane, aromatic hydrocarbons such as benzene, toluene and xylene, aliphatic hydrocarbons such as petroleum ether, hexane and methyl cyclohexane, ethers such as diethyl ether, tetrahydrofuran and dioxane, and alcohols such as isopropyl alcohol, tert-butanol, methanol and ethanol. Others include water, acetonitrile, and dimethyl sulfoxide.

Among these, aprotic solvents having an amide bond, and mixed solvents including an aprotic solvent having an amide bond and other solvents are preferred. Aprotic solvents having an amide bond that can be used here include N-methyl-2-pyrrolidinone, N,N-dimethylacetamide, and N,N-dimethylformamide.

The reduction step can be realized seamlessly with the ring-closing step by using an aprotic solvent having an amide bond, and then adding a reducing agent to the reaction solution (reaction system) without isolating Compound (II) from the reaction solution. Because Compound (II) is unstable, the Compound (II) isolating step can be eliminated, and the yield of Compound (I) can be further improved.

The reaction temperature in the ring-closing step can be set according to the types of Compound (III), base and solvent that are used. However, it is usually from −100° C. to 200° C., and preferably from −50° C. to 100° C. The reaction time can be set according to the types of Compound (III), base and solvent that are used. However, it is usually from 0.1 hours to 3 days, and preferably from 0.5 hours to 12 hours.

Manufacturing Method for Compound (III)

There are no particular restrictions on the method used to manufacture Compound (III). However, Compound (III) is preferably obtained (in the sulfonylation step) by reacting a compound represented by General Formula (IV) (referred to as Compound (IV) below) with a sulfonyl chloride derivative represented by the following general formula: $R^3SO_2Cl$.

Formula 9

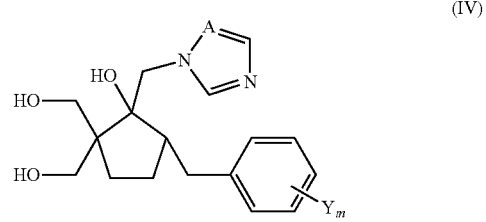

(IV)

In General Formula (IV), Y, m and A are the same as Y, m and A in General Formula (I), respectively.

The sulfonyl chloride derivative is a compound represented by $R^3SO_2Cl$. Here, $R^3$ is the same as $R^3$ in Compound (III). Among these, an alkyl group having 1 to 3 carbon atoms or a haloalkyl group having 1 to 3 carbon atoms is preferred. By using a sulfonyl chloride derivative such as an alkyl group having 1 to 3 carbon atoms or a haloalkyl group having 1 to 3 carbon atoms, a simultaneous sulfonylation reaction and cyclization reaction can be prevented, and the generation of compounds represented by General Formula (IIa) described in detail below can be inhibited. R³ being a methyl group is especially preferred.

The amount of sulfonyl chloride derivative used is usually from 0.5 to 10 times, and preferably from 1 to 5 times, the amount of Compound (IV) in terms of the mole ratio. The reaction may be performed without adding a base, but the addition of a base is preferred because it prevents the generation of hydrogen chloride. Here, the amount of base used is usually from 0 to 15 times (excluding 0 itself), and preferably from 1 to 10 times, the amount of Compound (IV) in terms of the mole ratio.

There are no particular restrictions on the base that can be used. Examples include alkali metal hydrogen compounds such as sodium hydride, potassium hydride and lithium hydride, and organic amines such as triethylamine, pyridine, N-methylimidazole, 4-dimethylaminopyridine and N,N-dimethyl aniline. From the standpoint of minimizing the generation of Compound (IIa), the use of organic amines such as triethylamine, pyridine, N-methylimidazole, 4-dimethylaminopyridine and N,N-dimethyl aniline is preferred.

Examples of solvents used in the reaction of the sulfonylation step include ethers such as 1,2-dimethoxyethane (DME), tetrahydrofuran and 1,4-dioxane, and amides such as N-methyl-2-pyrrolidinone as well as N,N-dimethylacetamide. These solvents can be used in a mixed solvent containing another solvent. Examples of other solvents that can be used in the mixture include halogenated hydrocarbons such as dichloromethane, chloroform and dichloroethane, aromatic hydrocarbons such as benzene, toluene and xylene, and aliphatic hydrocarbons such as petroleum ether, hexane and methyl cyclohexane. Others include acetonitrile and dimethyl sulfoxide.

The reaction temperature depends on the type of solvent and the type of base that are used. However, the reaction temperature is usually from −100° C. to 150° C., and preferably from −50° C. to 100° C. The reaction time also depends on the type of solvent and the type of base that are used. However, the reaction time is usually from 0.1 hours to several days, and preferably from 0.5 hours to 2 days.

When a sulfonylation reaction and ring-closing reaction occur simultaneously a compound represented by General Formula (IIa) (referred to as Compound (IIa) below) may be generated as a byproduct.

Formula 10

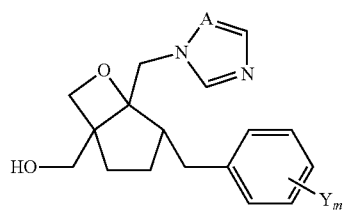

(IIa)

A reagent has to be added to derive Compound (II) from Compound (IIa). Because Compound (II) is an unstable compound, it is difficult to sulfonylate Compound (IIa) quantitatively. Therefore, Compound (II) is not obtained by performing the sulfonylation reaction and the ring-closing reaction in the same step. Instead, Compound (III) is manufactured first in the sulfonylation step, and Compound (II) is obtained by ring-closing Compound (III). In this way, generation of Compound (IIa) can be inhibited, and the amount of Compound (II) generated can be increased.

The method used to manufacture Compound (I) in the present embodiment can include a ring-closing step in which a compound represented by General Formula (II) is obtained by reacting a compound represented by General Formula (III) with a base.

The reduction step can be performed by adding a hydride-type reducing agent to the reaction system after the ring-closing step.

The method used to manufacture Compound (I) in the present embodiment can also include a sulfonylation step in which a compound represented by General Formula (III) is obtained by reacting a compound represented by General Formula (IV) with a sulfonyl chloride derivative represented by the General Formula: R³SO₂Cl.

Manufacturing Method for Compound (V)

The method used to manufacture Compound (I) in the present embodiment can be advantageously employed in the manufacture of azole derivatives represented by General Formula (V) (referred to as Compound (V) below). These azole derivatives are used as an active ingredient in agricultural and horticultural agents and in industrial material protecting agents.

Formula 11

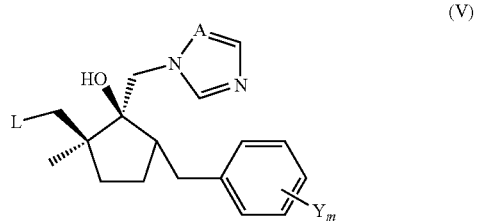

(V)

In General Formula (V), Y, m and A are the same as Y, m and A in General Formula (I), respectively, and L represents a halogen atom.

More specifically, a compound represented by General Formula (V) can be obtained by reacting a compound represented by General Formula (I) using the method describe above with a halogen acid and opening the ring. More specifically, Compound (I) can be mixed in a solvent with Compound H-L, and the oxetane ring in Compound (I) can be opened (ring-opening step) to generate a halogenated methyl group and a tertiary hydroxyl group and to obtain Compound (V).

Here, H-L represents a halogen atom. The halogen acid can be hydrogen chloride, hydrogen bromide, or hydrogen iodide. The halogen acid may be introduced as a gas, or may be dissolved in an organic solvent solution or aqueous solution and then added. Compound (V) may be obtained from Compound (I) by adding a halide salt and another type of acid (such as toluenesulfonic acid and methanesulfonic acid).

There are no particular restrictions on the solvent that can be used. Examples include amides such as N-methylpyrrolidone, N,N-dimethylacetamide and N,N-dimethylformamide, and ethers such as tetrahydrofuran and dioxane. A mixed solvent can be used which includes other solvents in addition to these. These solvents include halogenated hydrocarbons such as dichloromethane, chloroform and dichloroethane, aromatic hydrocarbons such as benzene, toluene and xylene, aliphatic hydrocarbons such as petroleum ether, hexane and methyl cyclohexane, ethers such as diethyl ether, tetrahydrofuran and dioxane, and alcohols such as isopropyl alcohol, tert-butanol, methanol and ethanol. Others include water, acetonitrile, and dimethyl sulfoxide.

The amount of Compound H-L used is usually from 0.5 to 100 times, and preferably from 1 to 30 times, the amount of Compound (I) in terms of the mole ratio.

The reaction temperature depends on the solvent and halogen acid that are used. However, the reaction temperature is usually from −20° C. to 250° C., and preferably from −10° C. to 150° C. The reaction time also depends on the solvent and the halogen acid that are used. However, the reaction time is usually from 0.1 hours to several days, and preferably from 0.5 hours to 2 days.

In the reduction method described in Patent Document 1, the reaction is performed in the presence of a sodium iodide halogenating agent in order to promote the reduction reaction using zinc (substitution of the sulfonic acid ester by an iodine atom). However, when Compound (I) is reacted with a halogen acid to open the ring and mixed with another halogenating agent in the reaction system (for example, an iodide such as sodium iodide or lithium iodide, or a bromide such as sodium bromide or lithium bromide when synthesizing Compound (V) in which L is a chloride atom), compounds other than Compound (V) may be generated as byproducts. When the compound to be generated includes a halogen atom other than the halogen atom in L in the reaction system manufacturing Compound (I), Compound (I) has to be purified and removed before the ring-opening reaction is performed.

However, the manufacturing method of the present embodiment can manufacture Compound (I) at a high yield without using a halogenating agent that substitutes a sulfonic acid ester with a halogen atom. Therefore, in relation to the synthesis of Compound (V), the ring-opening step can be realized seamlessly with the reduction step by adding a halogen acid to the reaction solution (reaction system) without isolating Compound (I) from the reaction solution in the reduction step. The Compound (I) isolating step can be eliminated, the manufacturing process can be simplified, and the yield of Compound (V) can be improved.

When realizing the ring-opening step seamlessly from the reduction step, Compound (II) is preferably reacted with a hydride-type reducing agent before adding water, an alcohol, an organic acid such as acetic acid, a mixture thereof, or a mixed solution containing an inorganic acid such as sulfuric acid therewith in the reaction solution (reaction system). In a reduction reaction performed on Compound (II) with a hydride-type reduction agent, a complex is believed to be formed by the reaction between the hydride-type reducing agent and Compound (II). When a halogen acid is added without water, an alcohol or an organic acid, byproducts are generated and the yield decreases. In order to avoid this, the complex can be dissociated by adding water, an alcohol or an inorganic acid. In this way, Compound (I) is generated as the reduction product, and then hydrogen halide addition and the ring-opening reaction can proceed efficiently. Therefore, the amount of Compound (I) present can be increased by adding water, an alcohol or an organic acid to the reaction system. This promotes the reaction used to obtain Compound (V) after the ring-opening reaction. As a result, the yield of Compound (V) can be improved.

The alcohol used here can be ethanol, methanol, isopropanol or t-butanol, and the organic acid can be an organic carboxylic acid such as acetic acid, propionic acid, trifluoroacetic acid or trichloroacetic acid, or an organic sulfonic acid such as mesylic acid or p-toluenesulfonic acid. The inorganic acid can be sulfuric acid, perchloric acid, phosphoric acid, phosphonic acid, phosphinic acid or nitric acid. A halogen acid such as hydrochloric acid, hydrobromic acid or hydroiodic acid can also be used as the inorganic acid. When a halogen acid is used, the ring-opening reaction can partially proceed, and halogen acid can mix with the compound converted into Compound (V). Therefore, when a halogen acid is used, the halogen acid preferably has the same halogen atom as L in Compound (V).

The halogen acid used in the ring-opening step may be added separately after water, an alcohol or an organic acid has been added and Compound (I) has been generated. It may also be dissolved before in water, an alcohol or an organic acid used to generate Compound (I). In this way, the manufacturing process can be simplified.

Examples are shown below in order to explain the embodiment of the present invention in greater detail. Of course, the present invention is not limited to these examples, and other modifications are possible regarding the details. The present invention is also not limited to the embodiment explained above. Other variations are possible within the spirit and scope of the present invention, and embodiments obtained by combining the present invention with previously disclosed technical means are included within the technical scope of the present invention. Furthermore, all documents described herein are incorporated by reference.

EXAMPLES

Example 1

Synthesis (I) of 5-(4-chlorobenzyl)-2-chloromethyl-2-methyl-1-(1H-1,2,4-triazolyl-1-ylmethyl)cyclopentanol (Compound (5))

In the following example, Compound (5) was synthesized using Reaction Scheme 1 below.

Reaction Scheme 1

Formula 12

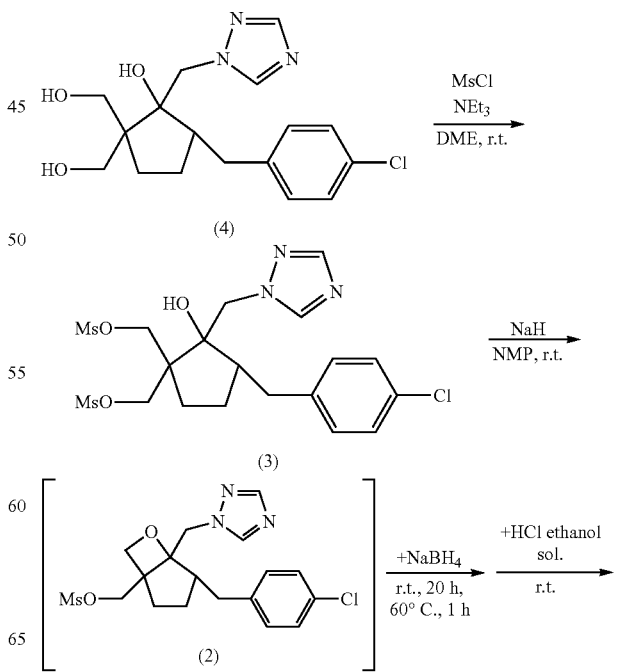

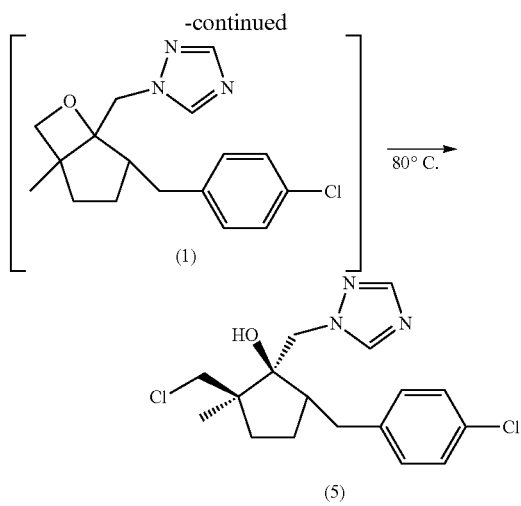

1,2,4-triazolyl-1-ylmethyl)cyclopentanol and (1RS,2SR, 5RS)-5-(4-chlorobenzyl)-2-chloromethyl-2-methyl-1-(1H-1,2,4-triazolyl-1-ylmethyl)cyclopentanol.

The $^1$H-NMR spectrum of Compound (5) obtained here matched the values of the $^1$H-NMR spectrum of the corresponding compound disclosed in Patent Document 1.

Yield (Amount): 0.373 g (Yield Percentage From Compound (3): 71%).

Example 2

Synthesis (I) of 4-(4-chlorobenzyl)-1-methyl-5-(1H-1,2,4-triazol-1-ylmethyl)-6-oxabicyclo[3,2,0]heptane) (Compound (1))

In the following example, Compound (1) was synthesized using Reaction Scheme 2 below.

Reaction Scheme 2

Formula 13

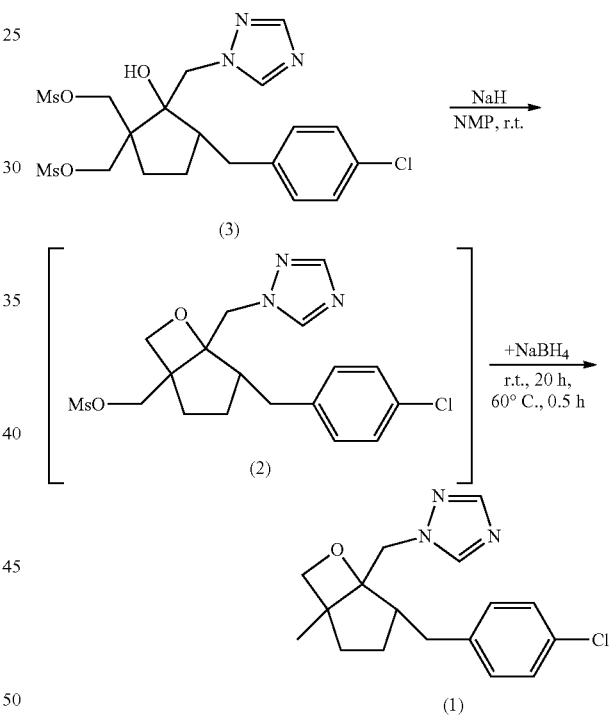

(1) Synthesis of [3-(4-chlorobenzyl)-2-hydroxy-1-methylsulfonyloxymethyl-2-(1H-1,2,4-triazol-1-ylmethyl)cyclopentyl]methyl methanesulfonate (Compound (3))]

5-(4-chlorobenzyl)-2,2-bis(hydroxymethyl)-1-(1H-1,2,4-triazol-1-ylmethyl)cyclopentanol (0.50 g, 1.42 mmol) (Compound (4)) and triethyl amine (0.70 ml, 1.42×3.5 mmol) were dissolved in DME (15 ml). After adding mesyl chloride (0.30 ml, 1.42×2.7 mmol) under ice-cooling, the solution was removed from the ice bath and stirred for 5 hours at room temperature. After the stirring was complete, 1N aqueous solution of hydrochloric acid was added and then extracted using ethyl acetate. After washing the organic layer using a saturated aqueous solution of sodium bicarbonate and a saturated aqueous solution of sodium chloride, the organic layer was dried using anhydrous sodium sulfate and then concentrated. The concentrate was refined using a silica gel column to obtain white, viscous Compound (3).

Yield (Amount): 0.688 g (Percentage: 95%).

(2) Synthesis of Compound (5)

Compound (3) (0.75 g, 1.48 mmol) was dissolved in NMP (5 ml), NaH (0.065 g (ca. 60% in mineral oil), 1.48×1.1 mmol) was added, and the solution was stirred for 1 hour at room temperature. NaBH$_4$ (0.084 g, 1.48×1.5 mmol) was added to the reaction solution, and the solution was stirred for 20 hours at room temperature and then allowed to react for 1 hour at approximately 60° C. The reaction solution was ice-cooled, 20.5% ethanol solution of hydrogen chloride (2.0 g, 0.00148×7.6 mol) was added, and the solution was stirred for 1 hour. Afterwards, the solution was removed from the ice bath and stirred another 1 hour. Next, 20.5% ethanol solution of hydrogen chloride (4.0 g, 1.48×15 mmol) was added and the solution was stirred for 2 hours. It was then stirred for another 1 hour at approximately 80° C. After the stirring was complete, water was added and then extracted using ethyl acetate. After washing the organic layer using water and a saturated aqueous solution of sodium chloride, the organic layer was dried using anhydrous sodium sulfate and then concentrated. The concentrate was refined using a silica gel column to obtain colorless, viscous Compound (5). Compound (5) obtained in this way was a mixture of (1RS,2SR,5SR)-5-(4-chlorobenzyl)-2-chloromethyl-2-methyl-1-(1H-

Compound (3) (0.75 g, 1.48 mmol) was dissolved in NMP (7 ml), NaH (0.072 g (ca. 60% in mineral oil), 1.48×1.2 mmol) was added, and the solution was stirred for 30 minutes at room temperature. NaBH$_4$ (0.168 g, 1.48×3.0 mmol) was added to the reaction solution, and the solution was stirred for 20 hours at room temperature and then allowed to react for 0.5 hours at approximately 60° C. Next, 10 wt % aqueous solution of sulfuric acid (10 ml) was added and the solution was stirred for 1 hour. Afterwards, water was added and then extracted using ethyl acetate. After washing the organic layer using an aqueous solution of sodium bicarbonate, water and a saturated aqueous solution of sodium chloride, the organic layer was dried using anhydrous sodium sulfate and then concentrated. The concentrate was refined using a silica gel column to obtain Compound (1).

Yield (Amount): 0.371 g, Yield (Percentage): 79%, White Solid.

Example 3

Synthesis (II) of Compound (1)

In the following example, Compound (1) was synthesized using Reaction Scheme 3 below.

Example 4

Synthesis (III) of Compound (1)

In the following example, Compound (1) was synthesized using Reaction Scheme 4 below.

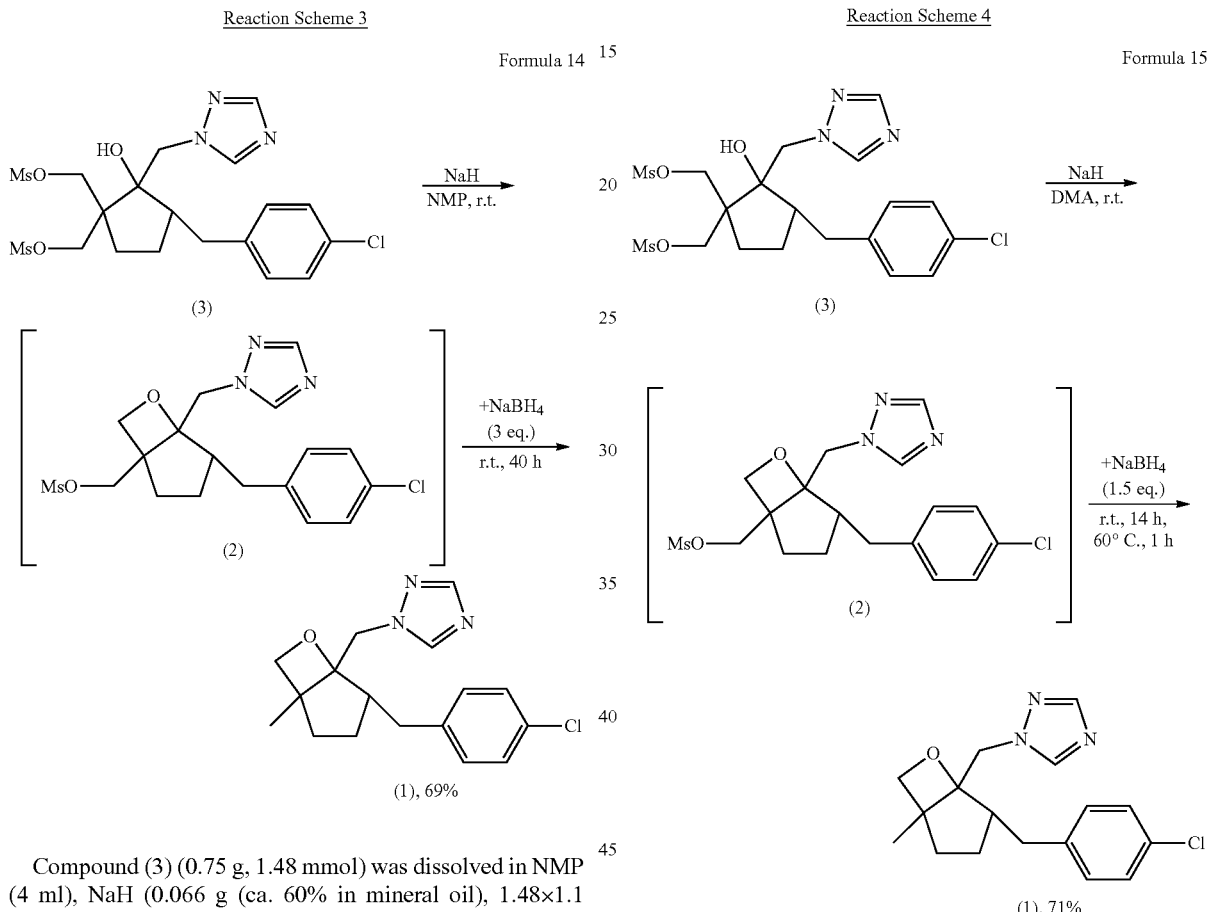

Compound (3) (0.75 g, 1.48 mmol) was dissolved in NMP (4 ml), NaH (0.066 g (ca. 60% in mineral oil), 1.48×1.1 mmol) was added, and the solution was stirred for 1 hour at room temperature. NaBH$_4$ (0.168 g, 1.48×3.0 mmol) was added to the reaction solution, and allowed to react for 40 hours at room temperature. Next, 48 wt % aqueous solution of sulfuric acid (2 ml) and water (8 ml) were added, and the solution was stirred for 3 hours. MeOH (5 ml) was then added, and the solution was stirred for another 2.5 hours. Because the presence of a fraction believed to be a boron complex was confirmed by HPLC, 48 wt % aqueous solution of sulfuric acid (2 ml) and water (5 ml) were added, and the solution was stirred for 2 hours. Afterwards, water was added and then extracted using ethyl acetate. After washing the organic layer using an aqueous solution of sodium bicarbonate and a saturated aqueous solution of sodium chloride, the organic layer was dried using anhydrous sodium sulfate and then concentrated. The concentrate was refined using a silica gel column to obtain Compound (1).

Yield (Amount): 0.324 g, Yield (Percentage): 69%, White Solid.

Compound (3) (0.75 g, 1.48 mmol) was dissolved in DMA (4 ml), NaH (0.066 g (ca. 60% in mineral oil), 1.48×1.1 mmol) was added, and the solution was stirred for 1 hour at room temperature. NaBH$_4$ (0.084 g, 1.48×1.5 mmol) was added to the reaction solution, allowed to react for 14 hours at room temperature, and then reacted for 1 hour at approximately 60° C. Next, 48 wt % aqueous solution of sulfuric acid (2 ml) and water (8 ml) were added, and the solution was stirred for 7 hours. Afterwards, water was added and then extracted using ethyl acetate. After washing the organic layer using a saturated aqueous solution of sodium bicarbonate and a saturated aqueous solution of sodium chloride, the organic layer was dried using anhydrous sodium sulfate and then concentrated. The concentrate was refined using a silica gel column to obtain Compound (1).

Yield (Amount): 0.335 g, Yield (Percentage): 71%, White Solid.

Example 5

Synthesis (IV) of Compound (1)

In the following example, Compound (1) was synthesized using Reaction Scheme 5 below.

Example 6

Synthesis (V) of Compound (1)

In the following example, Compound (1) was synthesized using Reaction Scheme 6 below.

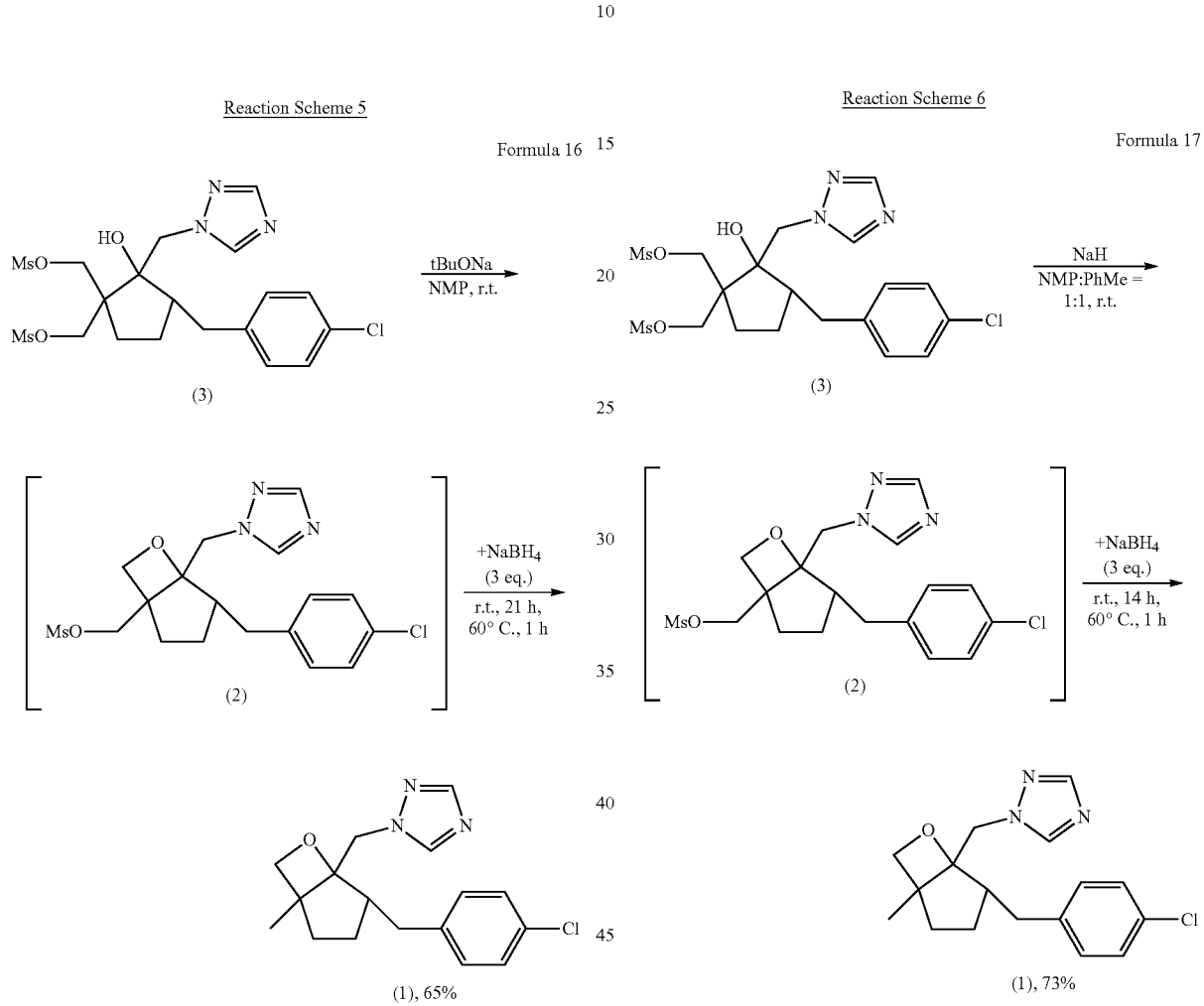

Compound (3) (0.50 g, 0.984 mmol) was dissolved in NMP (4 ml), sodium t-butoxide (tBuONa) (0.11 g, 0.984×1.2 mmol), and the solution was stirred for 1 hour at room temperature. NaBH$_4$ (0.112 g, 0.984×3.0 mmol) was then added to the reaction solution and it was allowed to react for 21 hours at room temperature. Afterwards, it was reacted for 1 hour at approximately 60° C. Next, 48 wt % aqueous solution of sulfuric acid (2 ml) and water (4 ml) were added, and the solution was stirred for 3.5 hours. Afterwards, water was added and then extracted using ethyl acetate. After washing the organic layer using a saturated aqueous solution of sodium bicarbonate and a saturated aqueous solution of sodium chloride, the organic layer was dried using anhydrous sodium sulfate and then concentrated. The concentrate was refined using a silica gel column to obtain Compound (1).

Yield (Amount): 0.205 g, Yield (Percentage): 65%, White Solid.

Compound (3) (0.50 g, 0.984 mmol) was dissolved in a mixed solvent of NMP (2 ml) and toluene (2 ml), NaH (0.044 g (ca. 60% in mineral oil), 0.984×1.1 mmol) was added, and the solution was stirred for 1 hour at room temperature. NaBH$_4$ (0.056 g, 0.984×1.5 mmol) was then added to the reaction solution and it was allowed to react for 14 hours at room temperature. Afterwards, it was reacted for 1 hour at approximately 60° C. Next, 48 wt % aqueous solution of sulfuric acid (2 ml) and water (4 ml) were added, and the solution was stirred for 3 hours. Afterwards, water was added and then extracted using ethyl acetate. After washing the organic layer using a saturated aqueous solution of sodium bicarbonate and a saturated aqueous solution of sodium chloride, the organic layer was dried using anhydrous sodium sulfate and then concentrated. The concentrate was refined using a silica gel column to obtain Compound (1).

Yield (Amount): 0.227 g, Yield (Percentage): 73%, White Solid.

Example 7

Synthesis (II) of Compound (5)

In the following example, Compound (5) was synthesized using Reaction Scheme 7 below.

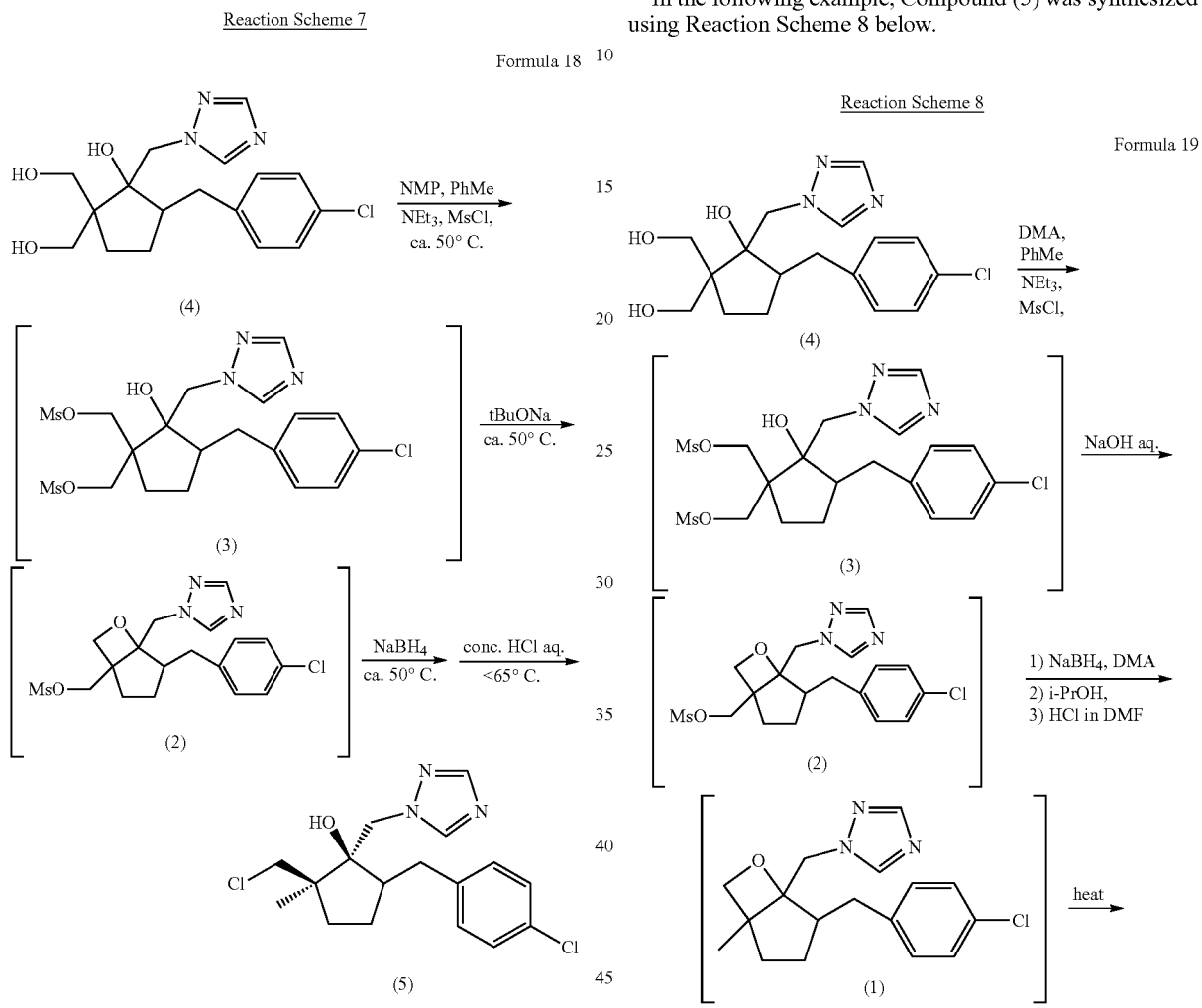

5-(4-chlorobenzyl)-2,2-bis(hydroxymethyl)-1-(1H-1,2,4-triazol-1-ylmethyl)cyclopentanol (0.70 g, 1.99 mmol) (Compound (4)) was dissolved in a mixed solution of NMP (5 ml) and toluene (5 ml). Triethyl amine (0.70 ml, 1.99×2.5 mmol) was added, the temperature was raised to approximately 45° C., mesyl chloride (0.32 ml, 1.99×2.1 mmol) was added, and the solution was allowed to react for 30 minutes at approximately 50° C. tBuONa (0.65 g, 1.99×3.4 mmol) was added to the reaction solution, and the solution was allowed to react for 30 minutes at approximately 50° C. Next, NaBH$_4$ (0.15 g, 1.99×2.0 mmol), and the solution was allowed to react for 3 hours at approximately 50° C. After adding concentrated hydrochloric acid (5 ml) to the reaction solution, the solution was allowed to react for 4 hours at approximately 50° C. Water was added to the reaction solution and then extracted using toluene. After washing the organic layer using a 2N aqueous hydrochloric acid, water and a saturated aqueous solution of sodium bicarbonate, the organic layer was dried using anhydrous sodium sulfate and then concentrated. The concentrate was refined using a silica gel column to obtain Compound (5).

Yield (Amount): 0.297 g, Yield (Percentage): 42%, White Solid.

Example 8

Synthesis (III) of Compound (5)

In the following example, Compound (5) was synthesized using Reaction Scheme 8 below.

Compound (4) (1.00 g, 2.84 mmol) and DMA (2 ml) were dissolved in toluene (5 ml), and triethyl amine (1.0 ml, 2.84× 2.5 mmol) was added. Mesyl chloride (0.46 ml, 2.84×2.1 mmol) was added at a temperature lower than 40° C., and the solution was stirred for 0.5 hours at room temperature. Next, 25% aqueous solution of sodium hydroxide (1.4 ml, 2.84×4.0 mmol) was added, and the solution was stirred for 1 hour at room temperature. Water was added to the reaction solution and then extracted using toluene. The organic layer was washed using water. DMA (3 ml) was added to the organic layer, and the low boiling-point substances were removed.

Next, NaBH$_4$ (0.118 g, 2.84×1.1 mmol) was added to the reaction solution, and allowed to react for 2 hours at approximately 55° C. Isopropanol (1.1 ml, 2.84×5 mmol) was added while water-cooling the reaction solution, and the solution was stirred for 1 hour at approximately 45° C. After stirring the solution, 4N DMF hydrogen chloride solution (3.6 ml, 2.84×5 mmol) was added, the solution was stirred for 1 hour at approximately 45° C., and the solution was then allowed to react for 4 hours at approximately 65° C. After the stirring was complete, water was added and then extracted using ethyl acetate. After washing the organic layer using water and a saturated aqueous solution of sodium chloride, the organic layer was dried using anhydrous sodium sulfate and then concentrated. The concentrate was refined using a silica gel column to obtain white, solid Compound (5). Compound (5) obtained in this way was a mixture of (1RS,2SR,5SR)-5-(4-chlorobenzyl)-2-chloromethyl-2-methyl-1-(1H-1,2,4-triazolyl-1-ylmethyl)cyclopentanol and (1RS,2SR,5RS)-5-(4-chlorobenzyl)-2-chloromethyl-2-methyl-1-(1H-1,2,4-triazolyl-1-ylmethyl)cyclopentanol.

The $^1$H-NMR spectrum of Compound (5) obtained here matched the values of the $^1$H-NMR spectrum of the corresponding compound disclosed in Patent Document 1.

Yield (Amount): 0.758 g (Yield Percentage From Compound (4): 75%).

Example 9

Synthesis (VI) of Compound (1)

In the following example, Compound (1) was synthesized using Reaction Scheme 9 below.

Reaction Scheme 9

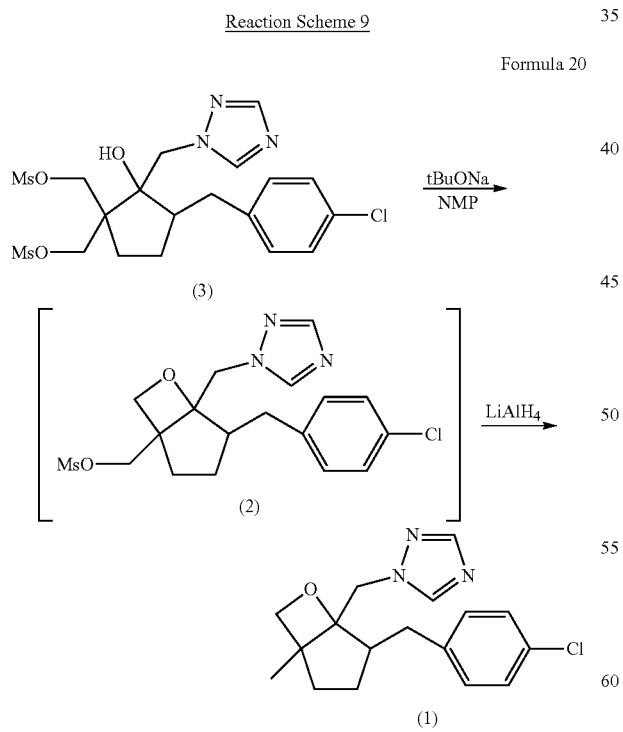

Compound (3) (0.80 g, 1.57 mmol) was dissolved in NMP (5 ml), t-BuONa (0.17 g, 1.57×1.1 mmol) was added, and the solution was stirred for 0.5 hours at room temperature. LiAlH$_4$ (0.144 g, 1.57×2.4 mmol) was added under ice-cooling in an argon atmosphere, and the solution was stirred for 0.5 hours. Next, the solution was removed from the ice bath, allowed to react for 18 hours at room temperature, and then reacted for 1 hour at approximately 50° C. Next, LiAlH$_4$ (0.072 g, 1.57×1.2 mmol) was added, the solution was stirred for 6 hours at the same temperature, and then stirred for 1 hour at 60° C. The reaction solution was poured into 25 wt % sulfuric acid aqueous solution (20 ml) to stop the reaction, and extracted using ethyl acetate. After washing the organic layer using a saturated aqueous solution of sodium bicarbonate and a saturated aqueous solution of sodium chloride, the organic layer was dried using anhydrous sodium sulfate and then concentrated. The concentrate was refined using a silica gel column to obtain Compound (1).

Yield (Amount): 0.185 g, Yield (Percentage): 37%, White Solid.

INDUSTRIAL APPLICABILITY

The present invention can be applied to the manufacture of 4-benzyl-1-methyl-6-oxabicyclo[3,2,0]heptane derivatives used as a raw material in agrochemicals.

The invention claimed is:

1. A method for manufacturing a compound represented by General Formula (I) below, the method comprising:
a step for reducing a compound represented by General Formula (II) below using a hydride-type reducing agent in (i) N-methyl-2-pyrrolidinone, (ii) N,N-dimethylacetamide, or (iii) a mixed solvent including at least N-methyl-2-pyrrolidinone or N,N-dimethylacetamide;

Formula 1

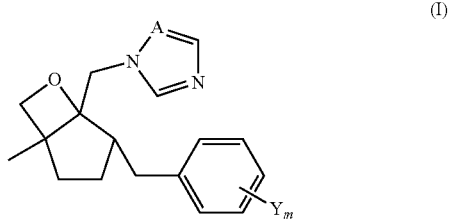

in General Formula (I), Y represents a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms, or a phenyl group, m represents an integer from 0 to 5, Y being the same or different when m is an integer equal to or greater than 2, and A represents a nitrogen atom or a methine group;

Formula 2

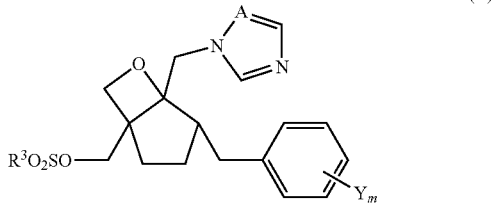

in General Formula (II), Y, m and A are the same as Y, m and A in General Formula (I), respectively, R3 represents an alkyl group having 1 to 3 carbon atoms or a haloalkyl group having 1 to 3 carbon atoms; and a ring-closing step for obtaining the compound represented by General Formula (II) above by reacting a compound represented by General Formula (III) below with a base;

Formula 3

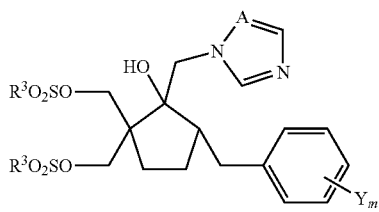

(III)

in General Formula (III), Y, m and A are the same as Y, m and A in General Formula (I), respectively, and R3 is the same as R3 in General Formula (II).

2. The manufacturing method according to claim 1, wherein the hydride-type reducing agent is a borohydride compound or an aluminum hydride compound.

3. The manufacturing method according to claim 1, wherein the hydride-type reducing agent is sodium borohydride, lithium borohydride, sodium trimethoxyborohydride, lithium aluminum hydride, or sodium bis(2-methoxyethoxy) aluminum hydride.

4. The manufacturing method according to claim 1, further comprising a reduction step for adding the hydride-type reducing agent to the reaction system after the ring-closing step.

5. The manufacturing method according to claim 1, further comprising a sulfonylation step for obtaining a compound represented by General Formula (III) above by reacting a compound represented by General Formula (IV) below with a sulfonyl chloride derivative represented by the general formula R3 SO2Cl (where R3 is the same as R3 in General Formula (III)):

Formula 4

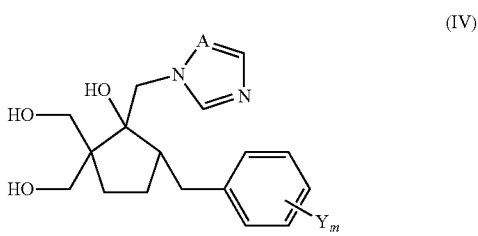

(IV)

in General Formula (IV), Y, m and A are the same as Y, m and A in General Formula (I), respectively.

6. The manufacturing method according to claim 1, wherein m in General Formula (I) above is an integer from 0 to 3, and Y is a halogen atom, an alkyl group having 1 to 3 carbon atoms, a haloalkyl group having 1 to 3 carbon atoms, an alkoxy group having 1 to 3 carbon atoms or a haloalkoxy group having 1 to 3 carbon atoms, and A represents a nitrogen atom when m is equal to or greater than 1.

7. The manufacturing method according to claim 1, wherein m in General Formula (I) above is an integer from 0 to 2, and Y represents a halogen atom and A represents a nitrogen atom when m is 1 or 2.

8. The manufacturing method according to claim 1, wherein R3 in General Formula (II) above represents a methyl group.

* * * * *